(12) United States Patent
Hallett

(10) Patent No.: US 6,728,583 B2
(45) Date of Patent: Apr. 27, 2004

(54) USER INTERFACE FOR A GAMMA CAMERA WHICH ACQUIRES MULTIPLE SIMULTANEOUS DATA SETS

(75) Inventor: Jeffrey A. Hallett, Livermore, CA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 375 days.

(21) Appl. No.: 09/894,285

(22) Filed: Jun. 27, 2001

(65) Prior Publication Data

US 2003/0004584 A1 Jan. 2, 2003

(51) Int. Cl.[7] .............................................. G05B 19/18
(52) U.S. Cl. ............................ 700/64; 700/17; 700/83; 700/59; 700/62; 600/407; 600/436; 345/419; 345/420; 345/424; 382/131; 250/370.08; 250/370.09; 250/369
(58) Field of Search .................... 700/17, 83, 19, 700/20, 56, 59, 60, 61, 62–64; 600/407, 436; 128/922; 378/901; 345/419, 418, 420, 424, 427; 382/131; 250/370.08, 370.09, 363.04, 369, 363.05

(56) References Cited

U.S. PATENT DOCUMENTS

| | | | | |
|---|---|---|---|---|
| 5,376,796 A | * | 12/1994 | Chan et al. ............ | 250/363.04 |
| 5,378,915 A | * | 1/1995 | Hines et al. ................ | 250/369 |
| 5,554,848 A | * | 9/1996 | Hermony et al. ....... | 250/363.05 |
| 5,629,971 A | * | 5/1997 | Jones et al. .................. | 378/145 |
| 5,682,036 A | * | 10/1997 | Hines et al. ........... | 250/363.09 |
| 5,760,402 A | * | 6/1998 | Hug et al. .............. | 250/363.05 |
| 5,803,914 A | * | 9/1998 | Ryals et al. ................. | 600/407 |
| 5,900,636 A | * | 5/1999 | Nellemann et al. ..... | 250/363.04 |
| 6,114,701 A | * | 9/2000 | Plummer et al. ....... | 250/363.04 |
| 6,150,662 A | * | 11/2000 | Hug et al. .............. | 250/363.08 |
| 6,288,397 B1 | * | 9/2001 | Maor ...................... | 250/363.05 |
| 6,359,279 B1 | * | 3/2002 | Gagnon et al. .......... | 250/363.1 |
| 6,459,086 B1 | * | 10/2002 | Kline et al. ............. | 250/370.13 |
| 6,525,323 B1 | * | 2/2003 | Vesel et al. .................. | 250/369 |
| 2003/0001099 A1 | | 1/2003 | Coles et al. | |
| 2003/0013950 A1 | * | 1/2003 | Rollo et al. ................. | 600/407 |

* cited by examiner

Primary Examiner—Ramesh Patel
(74) Attorney, Agent, or Firm—Eugene E. Clair

(57) ABSTRACT

A gamma camera system is described having a user interface by which protocols can be set up for the simultaneous acquisition of different views. Pull-down menus prevent the selection of incompatible simultaneous views for acquisition. The protocol being assembled, including its sequential steps and multiple simultaneous views, are displayed to the user.

13 Claims, 22 Drawing Sheets

PROCEDURE ID: GATED SPECT — 300

SPECT PARAMETERS

| | |
|---|---|
| DEGREES IN ORBIT: | 301 |
| IMAGES IN ORBIT: | 303 |
| MATRIX SIZE: | 305 |
| STARTING LOCATION: | 307 |
| ROTATION DIRECTION: | 309 |
| ORIENTATION: | 311 |
| ORBIT (CIRCULAR): | 313 |
| FLOOD CORRECTION: | 315 |
| ACQUISITION METHOD: | 317 |

ISOTOPE ID: 351
PATIENT ID: 353
VIEW ID: 355

PROCESSING 357

GATED PARAMETERS

| | |
|---|---|
| NO. OF GATED FRAMES | 331 |
| % R-R INTERVAL VARIANCE | |
| MAX % WINDOW | 333 |
| MIN % WINDOW | 335 |
| R-R INTERVAL FIXED | 337 |
| R-R INTERVAL VARY | 339 |
| NO. EXCLUDE AFTER VARIANCE | 341 |
| TIME PER ECT AZIMUTH OR TOTAL BEATS | 343 |

| | |
|---|---|
| TIME | AVG R-R |
| FRAME NO. | GATED FRAMES |
| MAX FRAME | MAX FRAMES |
| COUNTS/SEC | |
| BEATS | 365 |

USER INTERFACE FOR A GAMMA CAMERA WHICH ACQUIRES MULTIPLE SIMULTANEOUS DATA SETS

This invention relates to nuclear (gamma camera) imaging systems and, in particular, to gamma cameras which acquire multiple data sets simultaneously during a study.

When diagnosing a patient in a gamma camera study, the results of one study at times can determine whether another different study is required. For example, a cardiac study may acquire gated event data for imaging a particular phase of the heart cycle such as end-diastole. However, if the heartbeat is irregular, the acquired data set can be non-diagnostic, as it can be contaminated with event data acquired at times other than the desired phase of the heart cycle. In such a case the clinician may then decide to do an ungated study, where the irregular heartbeat is less of an obstacle to the intended data acquisition. This of course mandates a second study and may require a second dosing of the patient with the radionuclide. It would be desirable to be able to obviate the need for such subsequent studies so as to make more efficient use of the patient's time and the utilization of the gamma camera, and to obviate the need for repeated exposure of the patient to radionuclides.

Concurrently filed U.S. patent application Ser. No. 09/894,277 addresses this problem by providing a gamma camera system which acquires multiple data sets during a single study. The data sets are used to produce different types of images from the same protocol. If one type of image proves to be diagnostically unsuitable or ambiguous at the conclusion of the protocol, one of the alternate types of images may provide information which is better suited for making the diagnosis.

Since the multiple acquisitions are done during performance of the same protocol, the different acquisitions must be compatible with the same camera gantry behavior. The gamma camera system should automatically check for and prevent attempts to perform incompatible acquisitions simultaneously. Furthermore, these checks should occur as the clinician sets up the camera for the study. The user interface (control panel or display) of the camera should enable the clinician to set up a protocol uniquely designed for the patient and should allow the setting and editing of study parameters. Furthermore, the user interface should enable the setup of protocols which acquire multiple sets of image data simultaneously, thereby providing the clinician with a variety of diagnostic results.

In accordance with the principles of the present invention, a user interface is provided for a gamma camera system. The user interface enables a clinician to set up study protocols which have one or more sequential steps for automatic execution by the camera. Concurrently acquired views can be set up for a particular step in the protocol, and the user interface prevents setup of protocols with conflicting acquisition requirements. The user interface enables the clinician to set up different types of acquisitions concurrently without allowing the setup of protocols with conflicting simultaneous requirements.

IN THE DRAWINGS

FIG. 3 illustrates some of the parameters which may be used in a gated SPECT study;

FIGS. 7–12B illustrate user interface displays by which a clinician can set up proper protocols which perform different types of acquisitions concurrently.

Figure 1:
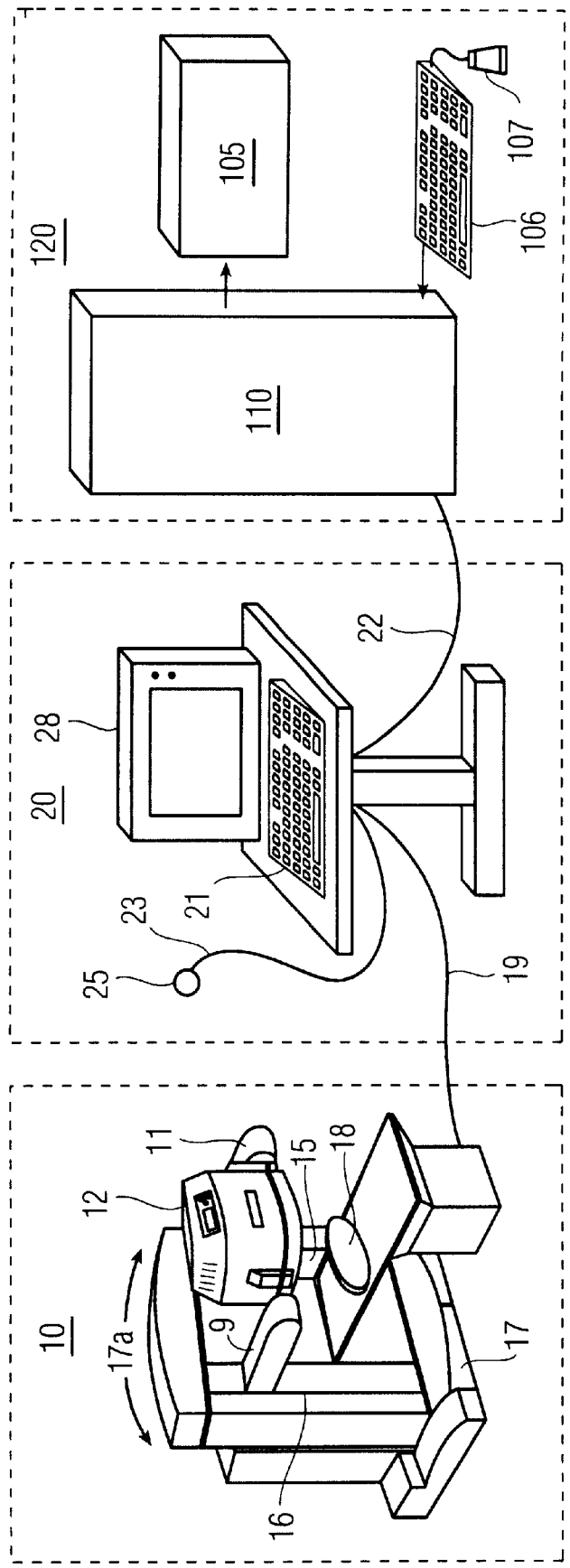
FIG. 1 illustrates the major components of a gamma camera system.

FIG. 1 illustrates the major components of a nuclear camera image acquisition, processing and display system. The present invention includes either a single head (single detector) camera 10 as shown in the drawing or a dual head (dual detector) camera as shown in U.S. Pat. No. 5,760,402 (Hug. et al.) or U.S. Pat. No. 6,150,662 (Hug et al.). These camera systems are SPECT cameras ideal for cardiac, abdominal, and whole body studies and are capable of implementing gated SPECT imaging techniques. In the illustration of FIG. 1, two arms 11 and 9 mounted on vertical tracks 16 and 15 form a gantry structure that can move the detector head 12 in various projection angles to accomplish the required 180 and 360 degree movements of the detector 12 used in gated SPECT studies. Pivot structure 17 allows the camera detector 12 and gantry structure to pivot clockwise or counterclockwise. The camera system 10 includes a detector head 12 comprising a number of well known radiation detection components of the Anger camera type including a photomultiplier array, a collimator, a scintillating crystal and a digital pixel output. The camera system 10, in a well known fashion, images the patient to provide digital image data which is binned according to particular discrete angles of rotation in which the detector 12 traverses about the patient. Binning can also occur according to particular phases of the cardiac cycle (R-R interval, defined below). For each angle of rotation, several phases of the cardiac cycle may be interrogated. Particular (x,y) coordinate positions within the imaging detector of the camera system are called pixel locations and the number of scintillations detected by each pixel location is represented by a count value for that pixel. Each pixel contains a count value representing the number of radiation emissions detected at that location of the detector 12. The resulting digital image data from the camera system 10 is binned according to the particular discrete angle of rotation in which the detector was situated when the image data was acquired. Also binned is the gated segment (phase) within the R-R interval in which the data was acquired in gated SPECT studies. The pixel matrix of (x,y) locations is referred to herein as a histogram of scintillations at these coordinate locations. It is understood that a histogram represents a raw image. For example, a typical detector 12 may have a resolution of (64×64) pixels or (128×128) pixels available for imaging and is capable of imaging at a maximum resolution of approximately (1000×1000) pixels.

The camera system 10 is coupled to a data acquisition computer system 20, which in a particular constructed embodiment is implemented using a general purpose computer system having high speed communications ports for input and output coupled to a two-way data transmission line 19 coupling the camera system 10 to the computer system 20. The computer system 20 communicates data acquisition parameters (also called data acquisition protocols) selected by a user to the camera system 10 to initiate a particular type of study by the camera system 10. The imaging data from the camera system 10 is then transferred over line 19 to the communications device of the system 20 and this raw gated SPECT image data is then forwarded to a post acquisition processing computer system 120. The data acquisition system 20 also comprises a keyboard entry device 21 for user interface to allow selection and modification of predefined data acquisition parameters which control the imaging processes of the camera system 10. Also coupled to the data acquisition system 20 is a standard color display monitor 28 for display of parameter information and relevant information regarding the particular gated SPECT study underway such as imaging status communicated from the camera system 10 during an imaging session.

For a gated SPECT study a cardiac electrode and signal amplification unit 25 is also coupled to the data acquisition computer system 20. This unit 25 is specially adapted to couple with a patient's chest near the heart to receive the heartbeat electrical signal. The unit 25 is composed of well known heartbeat detection and amplification (EKG) components and any of several well known devices can be utilized within the scope of the present invention. In order to perform gated SPECT analysis on the heart, the heartbeat pulse or electrical wave must be studied for each patient, as each heart is different. The heartbeat wave is examined to determine the points within the cycle where the well-known R wave is encountered. The time interval between successive R waves is measured to determine the R-R interval. These points and timing intervals between these points will be used to gate the imaging process of the camera system 10 during the cardiac cycle and particularly at the end-diastole and end-systole interval segments. The preferred embodiment of the present invention automatically, under control of the system 20, collects five sample heartbeat waves once the detector 25 is located on the subject patient in order to determine the average R-R period. This information is fed to the computer system 20 and then sent to the camera system 10. However such information could also be detected and determined directly by the computer system 10 once conditioned to do so by the acquisition computer system 20 under user control. For a particular projection angle, the system 10 directs the acquired imaging counts to the first segment bin, and upon each successive time interval the image data is directed to a new gated bin. When the R wave is detected once more, the first bin receives the image data again and the process continues through each other segment and associated bin until a new projection angle is encountered. The electrode 25 also is used by the camera system 10 in order to detect the start of a cardiac cycle and gate the camera imaging system appropriately depending on the number of selected segments of the R-R interval used for collection.

As discussed above, the data acquisition portion of the imaging system is composed of camera system 10 and computer system 20. Referring still to FIG. 1, the image data is sent from the camera system 10 over line 19 to acquisition system 20 and then over line 22 to the post acquisition processing system 120. This system 120 is responsible for processing, displaying and quantifying certain data acquired by system 10 and system 20. Specifically, the system 120 can process and uniquely display quantitative information regarding blood flow within the myocardium (perfusion) and wall motion of the myocardium (function) as a result of the gated SPECT data acquired.

The post acquisition processing system 120 acquires the raw gated SPECT image data generated by the camera system 10 and, using user configurable procedures, reconstructs (performs tomography or backprojection) the data to provide a reconstructed volume and from the volume generates specialized planar or volumetric images for diagnosis, including generating and displaying the functional images as described above. In cardiac imaging the generated images or frames represent different slices of the reconstructed heart volume at variable thicknesses in a short axis dimension, a vertical dimension and a horizontal dimension (all three are user configurable) for a number of gated time segments. Therefore, complete three dimensional information can be displayed by display 105 in a two dimensional manner in a variety of formats and orientations including a display providing quantitative information regarding both wall thickening (perfusion) and wall motion (function) of the myocardium under study.

Figure 2:
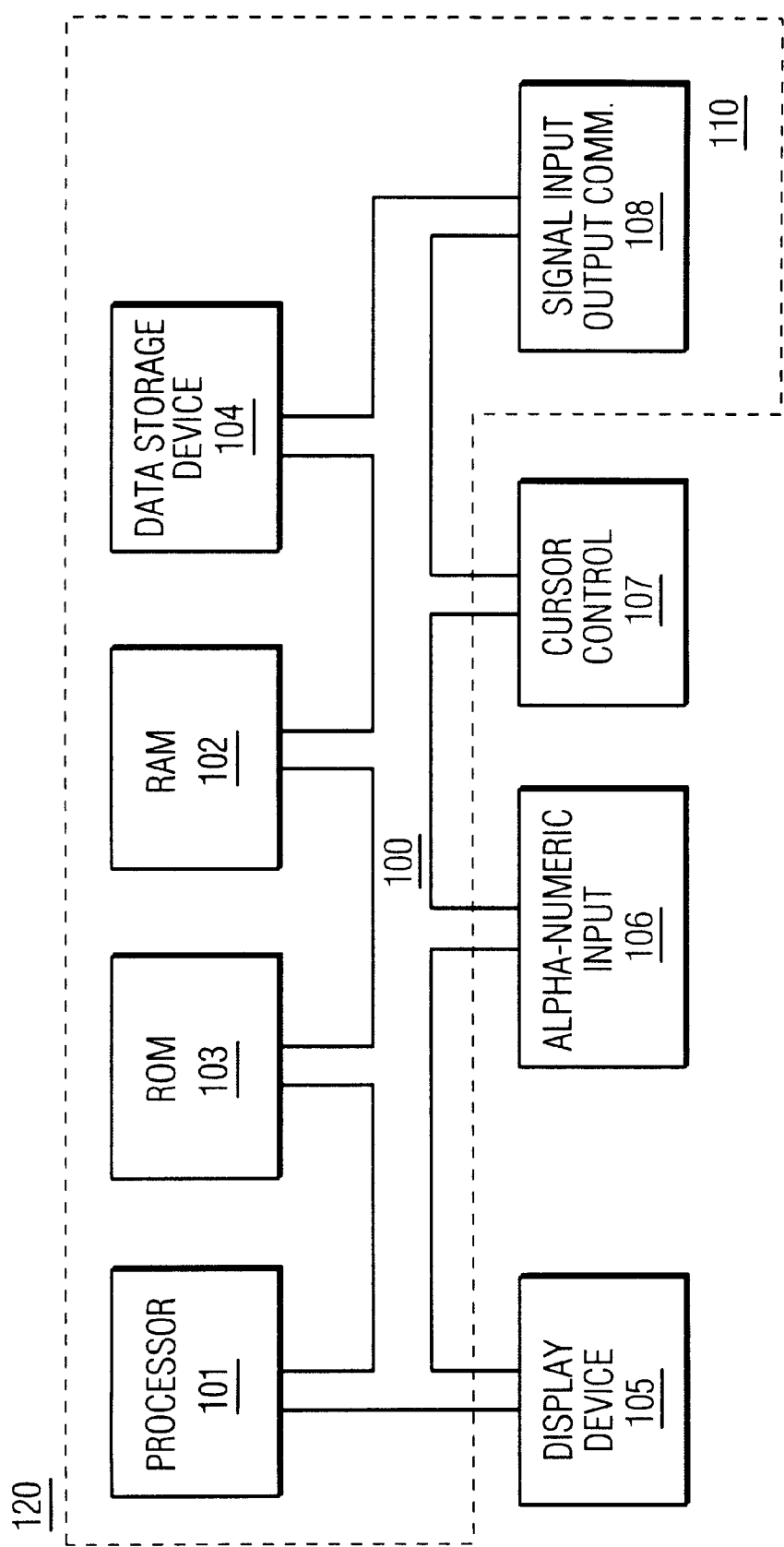
FIG. 2 illustrates in block diagram form the post data acquisition processing and display system of the gamma camera of FIG. 1.

The computer of the post acquisition processing system 120 in a constructed embodiment illustrated in FIG. 2 is a SPARC system available from Sun Microsystems of California, however any number of similar computer systems having the requisite processing power and display capabilities will suffice within the scope of the present invention. Generally, the system 120 comprises a bus 100 for communicating information, a central processor 101 coupled with the bus for processing information (such as image data and acquired counts) and command instructions, a random access memory 102 coupled with the bus 100 for storing information and instructions for the central processor 101, a read only memory 103 coupled with the bus 100 for storing static information and command instructions for the processor 101, a data storage device 104 such as a magnetic disk or optical disk drive coupled with the bus 100 for storing information (such as both raw gated SPECT and reconstructed data sets) and command instructions, and a display device 105 coupled to the bus 100 for displaying information to the computer user. There is also an alphanumeric input device 106 including alphanumeric and function keys coupled to the bus 100 for communicating information and command selections to the central processor 101, a cursor control device 107 coupled to the bus for communicating user input information and command selections to the central processor 101 based on hand movement, and an input and output device 108 coupled to the bus 100 for communicating information to and from the computer system 120. The input and output device 108 includes, as an input device, a high speed communication port configured to receive image data acquired by the nuclear camera system 10 and fed over line 22.

The display device 105 utilized with the system of the present invention may be a liquid crystal device, cathode ray tube, or other display device suitable for creating graphic images and alphanumeric characters recognizable to the user. The display unit 105 of the preferred embodiment of the present invention is a high resolution color monitor. The cursor control device 107 allows the computer user to dynamically signal the two dimensional movement of a visible symbol or cursor 5 (pointer) on a display screen of the display device 105. Many implementations of the cursor control device are known in the art including a trackball, mouse, joystick or special keys on the alphanumeric input device 105 capable of signaling movement of a given direction or manner of displacement. It will be appreciated that the cursor control device 107 also may be directed and/or activated via input from the keyboard using special keys and key sequence commands, or from a touchscreen display device. In the discussions regarding cursor movement and/or activation within the preferred embodiment, it is to be assumed that the input cursor directing device may consist of any of those described above and is not limited to the mouse cursor device. It will be appreciated that the computer chassis 110 may include the following components of the image processor system: the processor 101, ROM 103, RAM 102, the data storage device 104, and the signal input and output communication device 108 and optionally a hard copy printing device.

The data acquisition system 20 allows a user via keyboard control to select and/or create a predefined set of parameters (or protocols) for direction of a gated SPECT imaging session or other selected study by the camera system 10. FIG. 3 illustrates a parameter interface screen and configurable parameters of a nuclear camera system for data acquisition that are selected and displayed on a screen by the user via keyboard 21. FIG. 3 illustrates some of the parameters that are configurable by the data acquisition system 20. It is appreciated that once set, the configurable parameters can be saved and referenced in a computer file for subsequent recall. The stored parameters or protocol file can then be recalled and utilized for a particular study, thus eliminating the need to again enter the parameters for similar or identical studies. The name of the parameter file shown in FIG. 3 is "GATED SPECT" and is indicated at 300. It is appreciated that the computer system 20, once instructed by the user, will relay the parameters set by the user to the camera system 10 in order to initialize and begin a particular study. The initiation is done by selection of processing command 357. A user interface of this type is thus versatile while at the same time providing a high degree of automation of the execution of selected study protocols.

Figure 4:
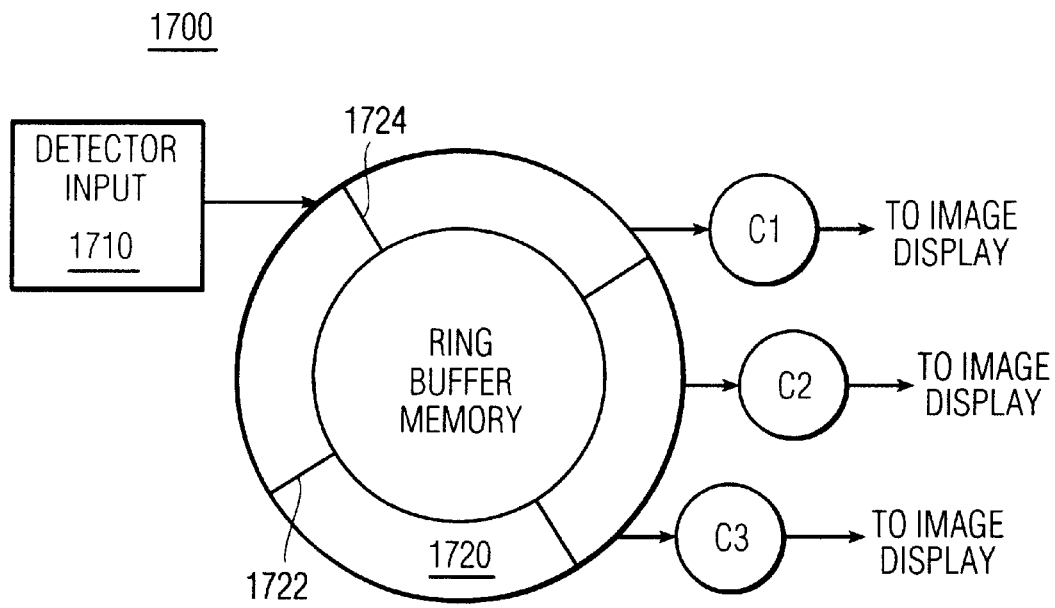
FIG. 4 illustrates in block diagram form a network of the gamma camera which simultaneously processes different data sets from the same imaging procedure in accordance with the principles of the present invention.

In accordance with the principles of the present invention, the gamma camera system of FIGS. 1–3 is capable of performing several studies simultaneously by use of the data network shown in FIG. 4. The network includes a ring buffer 1720 into which gamma camera data is entered at a high data rate. The data in the illustrated ring buffer 1720 may have a specified start point 1722 and an end point 1724 that may adjust around the ring buffer as data is received and processed. The gamma camera data is entered into the ring buffer by one or more Producers, one of which is shown at 1700. A Producer is a camera subsystem or data path which enters data into the ring buffer 1720. The Producer illustrated in the drawing is a data stream 1710 from a detector or camera head, which inputs detector data into the ring buffer. Other Producers may provide data from other sources such as stored data sources, for example. Some of the types of data words which are provided by a detector are described in FIG. 6 below.

Accessing the data which traverses the ring buffer 1720 are one or more Consumers. Three Consumers are shown in FIG. 4, and are labeled C1, C2, and C3. A Consumer is a data processor or path or other entity which makes use of some or all of the data in the ring buffer 1720. In the illustrated embodiment each Consumer is an entity conditioned to look for specific characteristics of event data and to read data from the ring buffer selected for a particular type of study. The studies in the following examples are all associated with types of images and hence the Consumers shown in this example read and process selected data into images, which can then be forwarded to an image display. Each Consumer C1, C2 and C3 examines the data in the ring buffer as it passes by its input, and independently reads those data words which are needed for the studies being supported by that Consumer. The Consumers operate both independently and simultaneously, and each can support one or more imaging processes.

Figure 5:
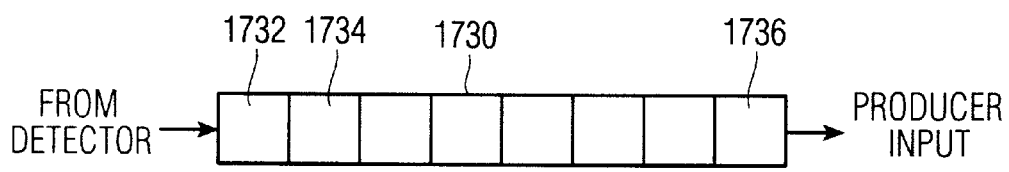
FIG. 5 illustrates a high speed data path from which the Producer of FIG. 4 reads input data.

In a constructed embodiment the data from a detector, being produced in real time as the detector head detects scintillation events, is provided over a high speed data path 1730 as illustrated in FIG. 5. The stream of data words is provided serially from the detector as indicated by sequential data locations 1732, 1734 . . . 1736. The data at the output of the data path 1730 is read by the input of a Producer, which enters the data into the ring buffer 1720.

Figure 6:
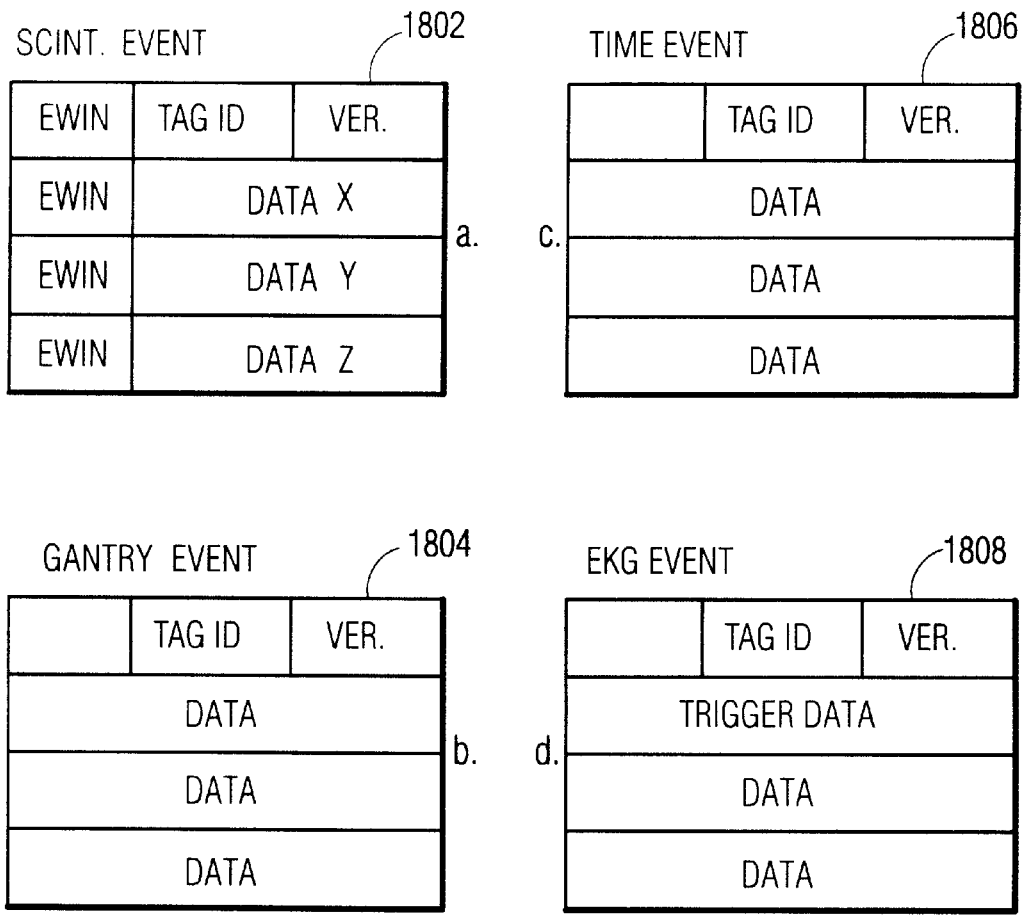
FIG. 6 illustrates the format of the data used in a constructed embodiment of the present invention.

Examples of the types of event data which may be provided by a detector are shown in FIG. 6. In this example each event word is 64 bits long. The words in this drawing are shown in four lines of sixteen bits each. FIG. 6a illustrates a scintillation event word 1802 with four energy window bytes EWIN of four bits each. The setting of one of these bits denotes one of sixteen energy windows in which the particular scintillation event was acquired. Typically a detector will only produce data for energy windows chosen by the camera operator. The TAG ID and TAG VERSION (VER.) bytes identify the data word as a scintillation event word. The TAG bytes provide information such as the detector number which produced the event. Data X and Data Y provide the x and y coordinate locations on the detector at which the event was sensed. The Data Z byte provides the energy number of the detected event.

FIG. 6b shows a format for a gantry event word 1804. Gantry event words provide information as to the current position of the gantry and hence the locations of the detectors. Gantry event data originates with sensors, controllers, and other devices associated with the gantry or from control programs for the gantry. The illustrated gantry event word 1804 has TAG ID and VER. bytes which identify the word as a gantry event word. The TAG bytes provide information as to the type of information contained in the gantry event word. The last three lines contain the data pertinent to the gantry event.

FIG. 6c gives an example of a time event word 1806. The acquisition system provides these words as time markers so that the other events of the camera can be oriented in time. Time events occur in regular intervals such as once every millisecond. The TAG bytes of the time event word denote the word as a time event word. The rest of the time event word comprises data giving the time information.

FIG. 6d illustrates an EKG event word 1808, which will be produced when a cardiac electrode unit 25 is used for a gated study. The TAG bytes identify the word as an EKG event word. A TRIGGER DATA byte provides information as to the trigger event, and the other data bytes of the EKG event word provide other information pertinent to the EKG event.

Other event words may also be present in the data stream provided by the detectors and entered into the ring buffer 1720. For example Start and Stop event words may be used to indicate the start of an image acquisition session and the conclusion of an image acquisition session.

Some examples will illustrate various studies which can be carried out simultaneously by an embodiment of the present invention. One example is imaging with two energy windows simultaneously. Consumer C1 is conditioned to look for scintillation event words in the ring buffer for which the EWIN#1 bit is set. Scintillation event data exhibiting this characteristic is selected and is binned to form pixels for a first image W1. Consumer C2 is conditioned to look for scintillation events in the ring buffer for which the EWIN#2 bit is set, and this scintillation event data is read by the Consumer C2 and binned to form pixels for a second image W2. A third Consumer C3 is conditioned to look for scintillation event words in which either bit EWIN#1 or bit EWIN#2 is set, and reads and bins this event data to produce pixels for a third image W1+W2. All three Consumers use gantry events and time events. A variation of this operation would be to use only a single Consumer to look for scintillation event words in which either bit EWIN#1 or bit EWIN#2 is set, and to thereafter sort and bin this event data into distinct images W1, W2, or W1+W2.

A second example of an application of the present invention is to perform gated and ungated studies simultaneously. Two Consumers C1 and C2 are separately conditioned for the two types of studies. In this example, Consumer C1 monitors the event data for EKG trigger event data, while Consumer C2 does not monitor this data. For example, C1 may be conditioned to acquire an image of data produced during a heart cycle interval occurring 600–700 milliseconds after the start of a heart cycle. The Consumer C1 would monitor the event data in the ring buffer until an EKG trigger event word is identified. Consumer C1 then begins reading scintillation event data and forwarding the event data to an image processor. When the count of time event words by C1 reaches the predefined time (600–700 milliseconds in this example), C1 stops binning the scintillation event words. Consumer C1 then monitors the event data for the next EKG event word, whereupon the process repeats for the next heart cycle.

While Consumer C1 is acquiring the gated heart data, Consumer C2 is acquiring ungated event data. For example, Consumer C2 may be conditioned to acquire scintillation event data continuously for 20 seconds, which covers many heart cycles. As Consumer C1 begins to monitor and acquire its gated acquisition data, the Consumer C2 acquires a continuous stream of event data for 20 seconds or 20 heart cycles, or some other selected period. Consumer C2 forwards the event data it selects to an image processor for binning of an ungated image.

This acquisition sequence, in which one Consumer acquires gated event data while another Consumer acquires ungated event data, is performed for each gantry position of the protocol. The simultaneous acquisitions are repeated for each gantry position based upon the detection of new gantry events by the Consumers. In a constructed embodiment the Consumers provide status of their acquisitions to a control program. When each Consumer has satisfied its needs for new event data at a particular gantry location, this status is reported to the control program. When all Consumers report that they are satisfied, the control program commands the movement of the gantry to the next detector position.

When acquisition data has been acquired from all of the gantry positions of the protocol, the study and its acquisition of the simultaneous images is complete. The clinician may find that the gated image is sufficient for a diagnosis and may make a diagnosis without examining the ungated image at all. Alternatively, the clinician may discover that the patient has experienced an irregular heartbeat during the study, and that this has caused the scintillation events to be inaccurately binned. The gated image may thus be nondiagnostic. The clinician can then examine the ungated image, which is not similarly affected by the irregular heartbeat. The ungated image may be sufficient for the clinician to conclude a diagnosis, which is thus made without conducting another study and without the need to redose the patient.

Other types of simultaneous studies are possible with an embodiment of the present invention. For instance, zoomed and unzoomed images may be produced simultaneously by conditioning the Consumers to select event data from the appropriate detector locations, and binning the event to the appropriate zoomed and unzoomed pixel resolution. As another example, both flow and wall motion images can be acquired simultaneously, as well as both perfusion and wall motion images.

One skilled in the art will appreciate that, since the simultaneous acquisitions are being made during the same sequence of gantry motion, the two acquisitions must be ones that can be performed during the extant gantry behavior. For example, a planar gated study (in which the detector head is stationary) and an ECT study (in which the detector head moves) cannot be performed simultaneously, since these two procedures call for different detector motion. Accordingly, the control program which sets up the simultaneous protocols at the outset of the exam performs consistency checks of the multiple acquisitions called for by the operator to assure that the two acquisitions utilize the same gantry behavior. In accordance with the principles of the present invention, a user interface which presents these features to the operator is described in FIGS. 7–12.

Figure 7:
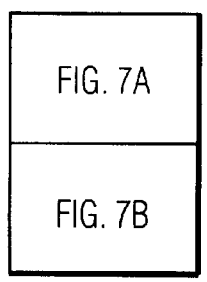
Figure 7A:
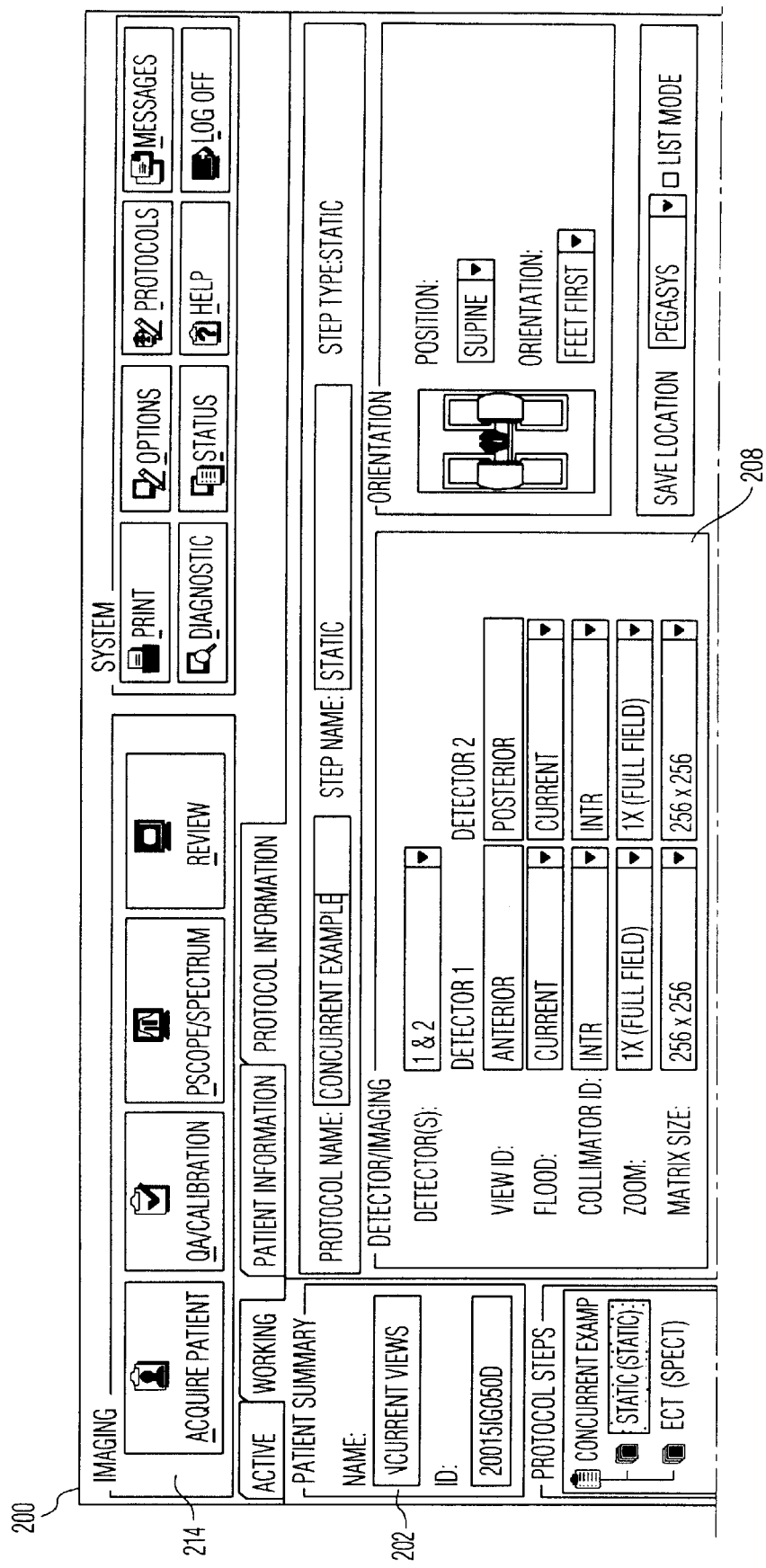
Figure 7B:
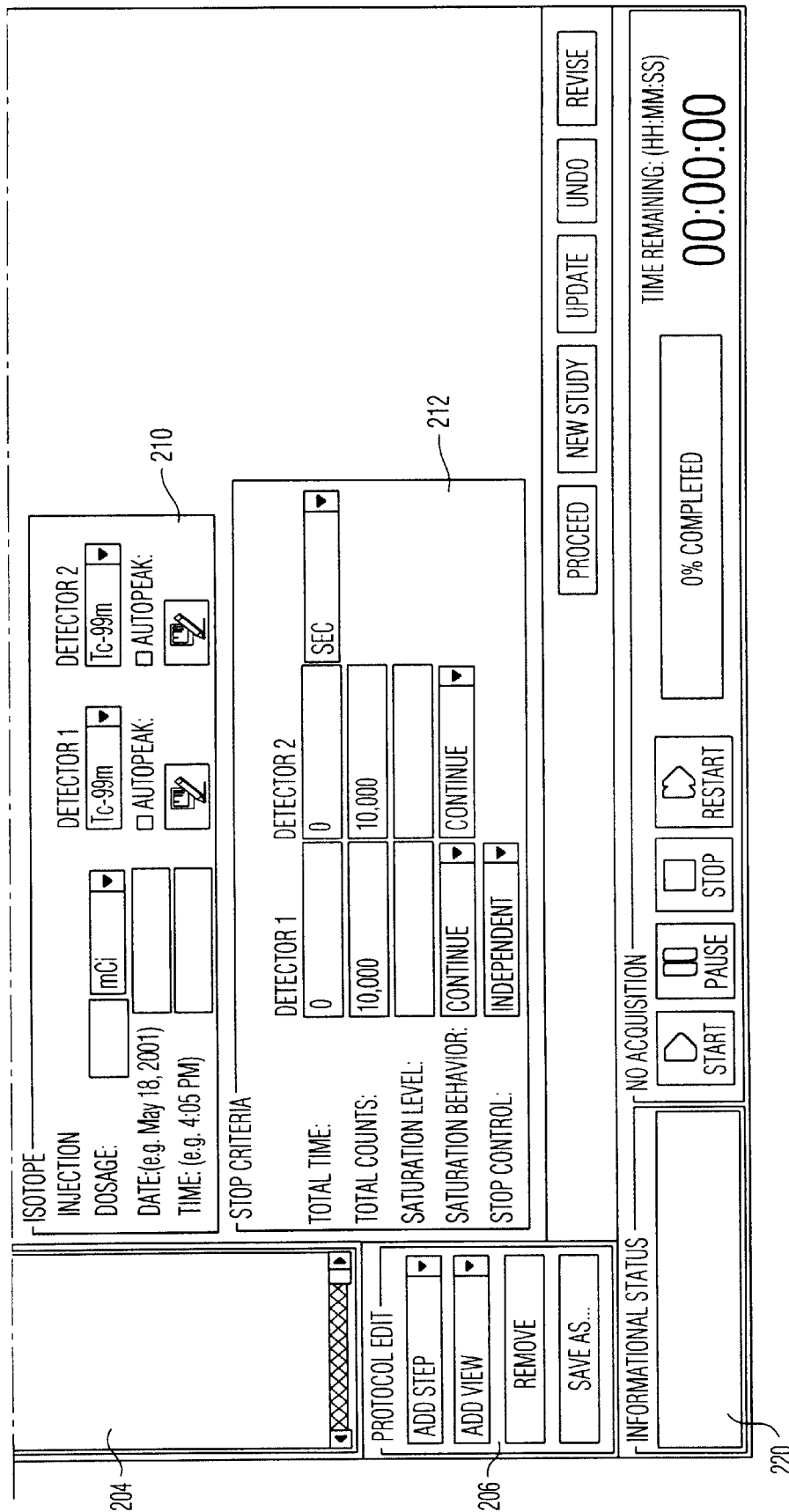

FIG. 7 illustrates a user interface screen 200 by which the operator of the gamma camera sets up a protocol. At the top of the display is a row 214 of control buttons, including one labeled "Acquire Patient." This button is clicked by the operator to command the camera to begin executing the protocol which has been set up by the operator. Below the row 214 of control button and on the left side of the screen is a display area 202 where the operator enters patient identification data. Below this area is a display area 204 where the steps of the protocol are displayed. A protocol may have one or more steps which are performed sequentially. In the illustrated example the protocol has a static step followed by an ECT (SPECT) step. During the static step the camera detector heads do not move, and during the SPECT step the detector heads are moved around the patient as radionuclide events are gathered. Below the protocol step area 204 is a protocol edit area 206 where the operator is given selections to add or remove steps or acquired views from the protocol. At the bottom of the screen is a status bar 220.

In the center of the screen are display areas 208, 210, and 212 which provide for the setting of details of the particular protocol being set up. The example shown in FIG. 7 is a protocol called "concurrent example" because it exemplifies a protocol where several views are acquired concurrently during one step of the protocol. Since the "Static" step is highlighted in display area 204, the center area of the screen displays and allows entry of information concerning the Static step of the Concurrent Example protocol. The Detector/Imaging area 208 is where parameters of the detector are entered. Information about the isotopes being used in the study is entered in area 210. In this example the isotope Tc-99m is being used in the static step of the protocol. Identification of the isotopes used aids in setting up and manipulating the energy windows used in the study. In Stop Criteria area 212 the operator enters parameters which will determine when the particular step of the protocol is ended. In this example event data is acquired for an image until 10,000 counts have been accumulated.

Figure 8A:
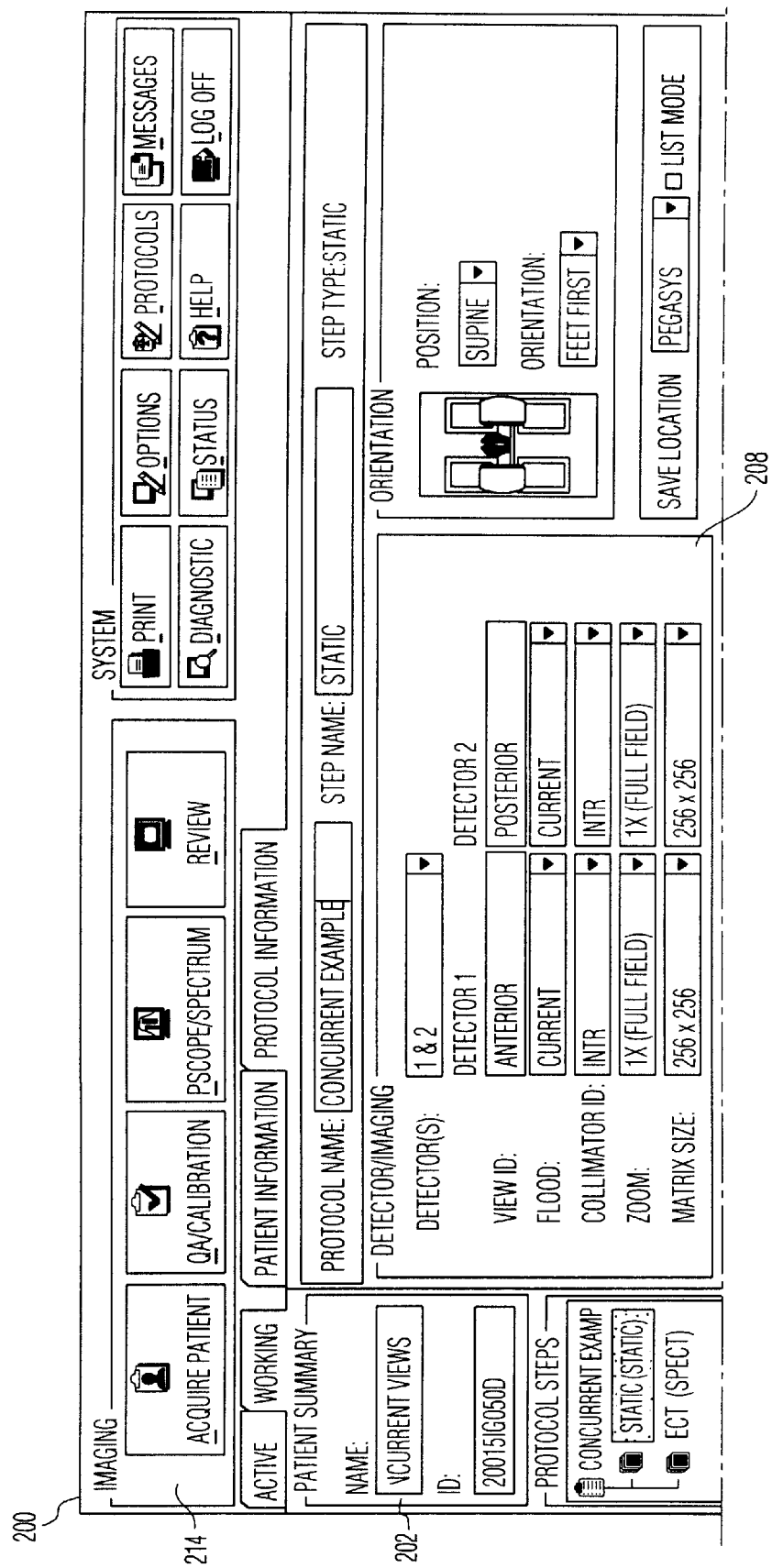
Figure 8B:
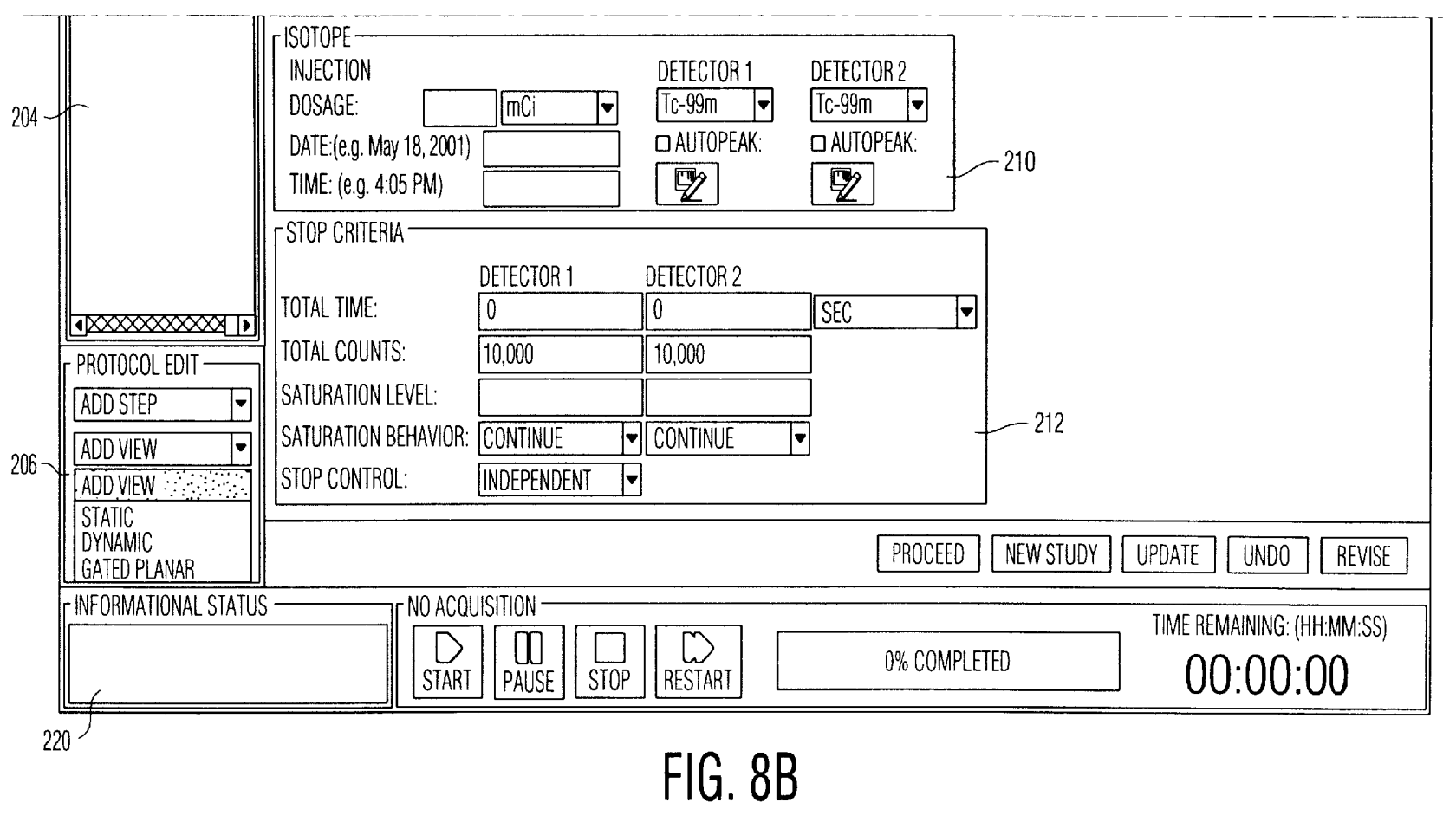

FIG. 8 shows how the operator adds another view to a step of the protocol. This is done by clicking on the pull-down "Add View" menu. In this example the operator is given the choice of adding a static, dynamic, or gated planar view to the Static step highlighted in the protocol box 204. By using pull-down menus instead of allowing data to be typed in, the user interface restricts additional views to those that are valid for the particular step being modified. The pull-down menu could display all views of the camera with incompatible ones greyed out. However, in the preferred embodiment the pull-down menu shows only those choices which are valid for the protocol step highlighted. This self-check mechanism is necessary for tasks being performed concurrently such as simultaneous image acquisition, but is not generally a concern for serial tasks such as the sequential steps of the protocol.

Figure 9:
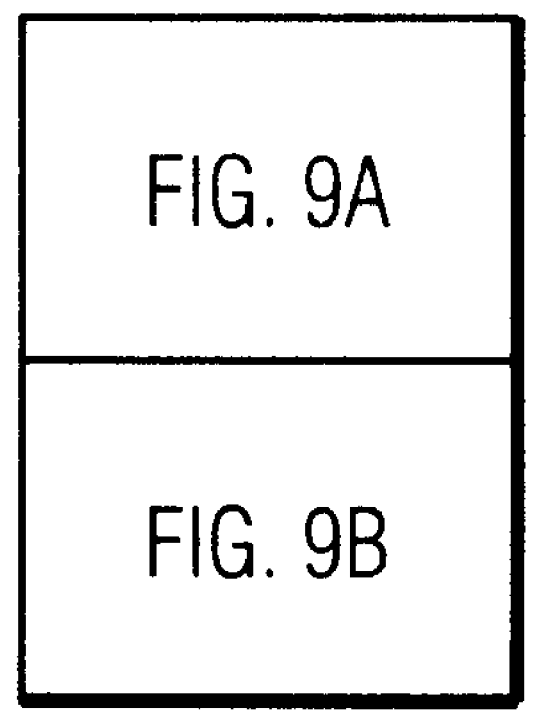
Figure 9A:
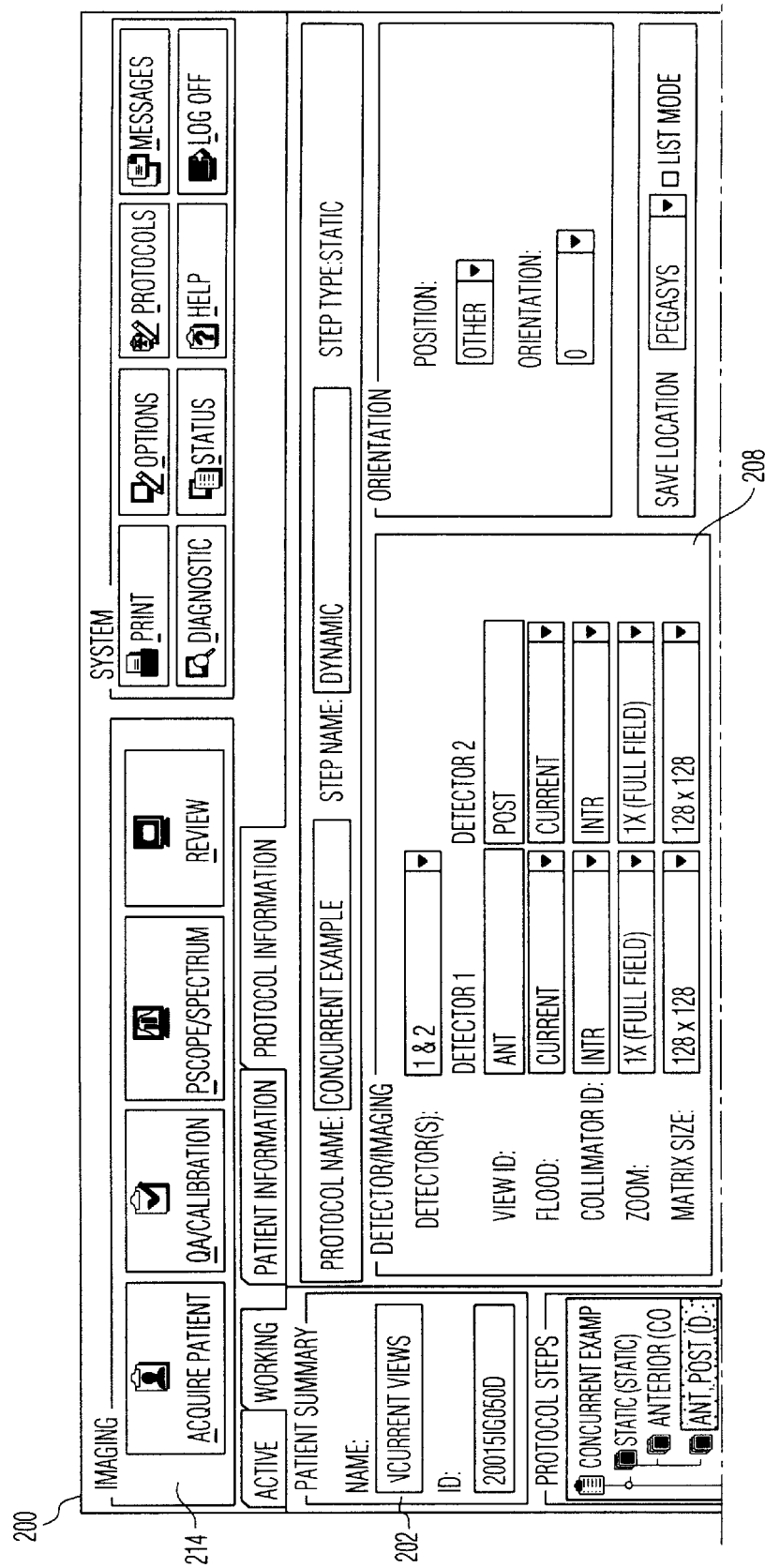
Figure 9B:
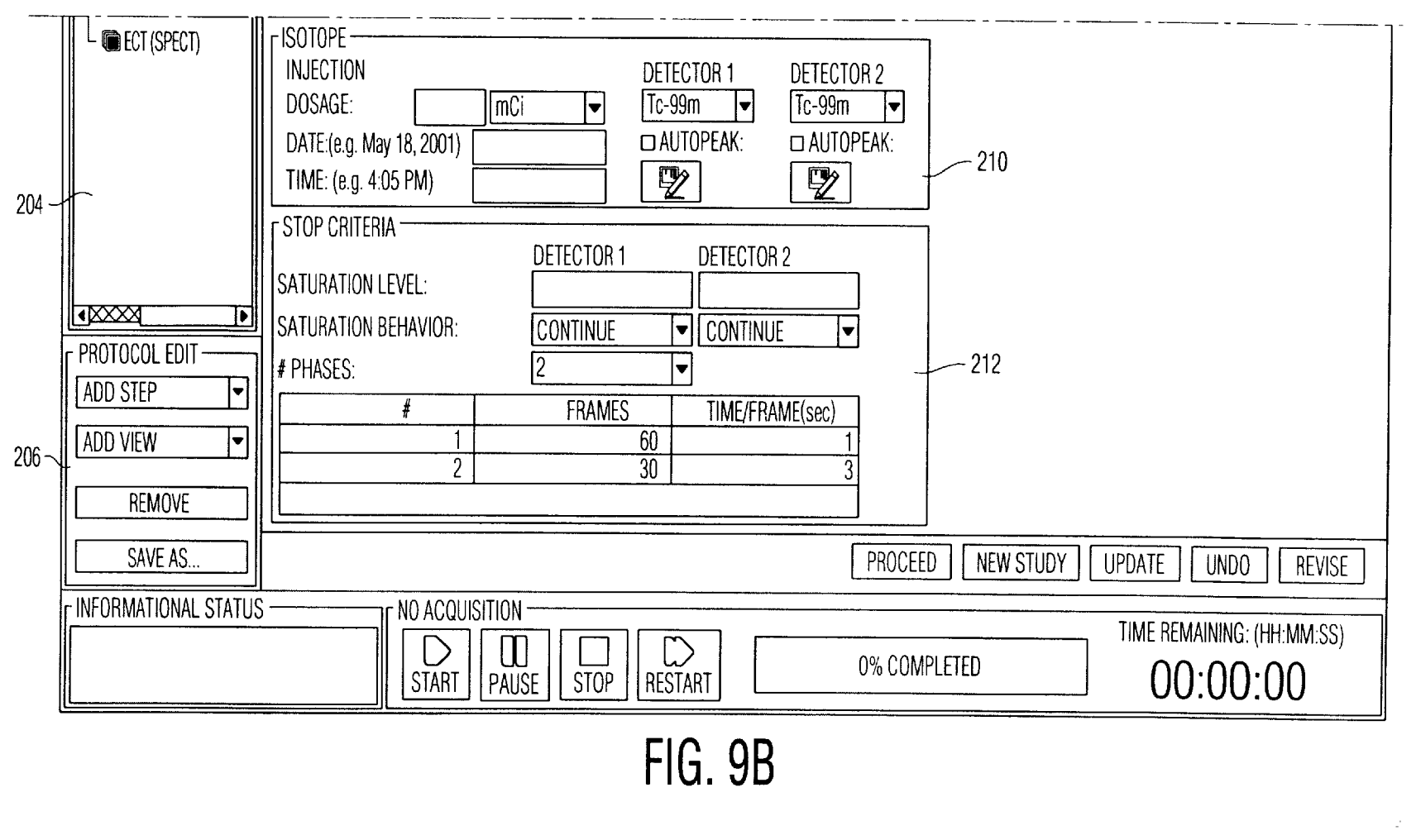

FIG. 9 shows the result of adding the acquisition of a concurrent dynamic view to the static step. Concurrent views are now shown beneath the Static step heading in the protocol box 204. Thus, during execution of the static step of the protocol, the camera will perform two different types of image data acquisition.

Figures 10, 10A, 10B:
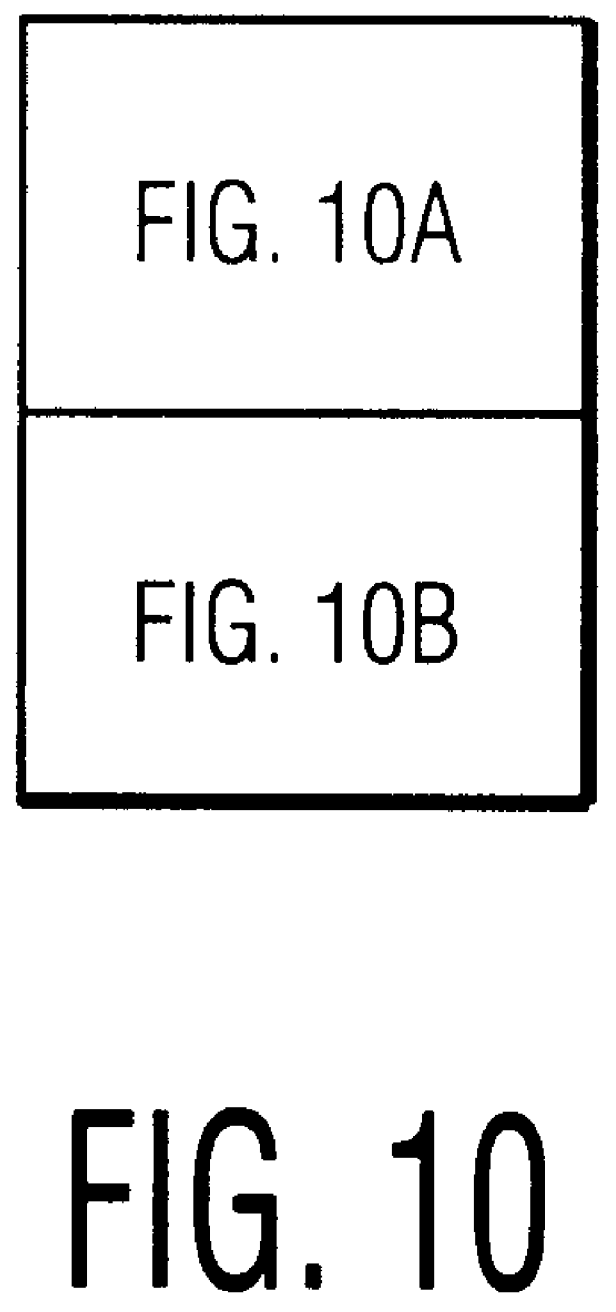
Figure 10A:
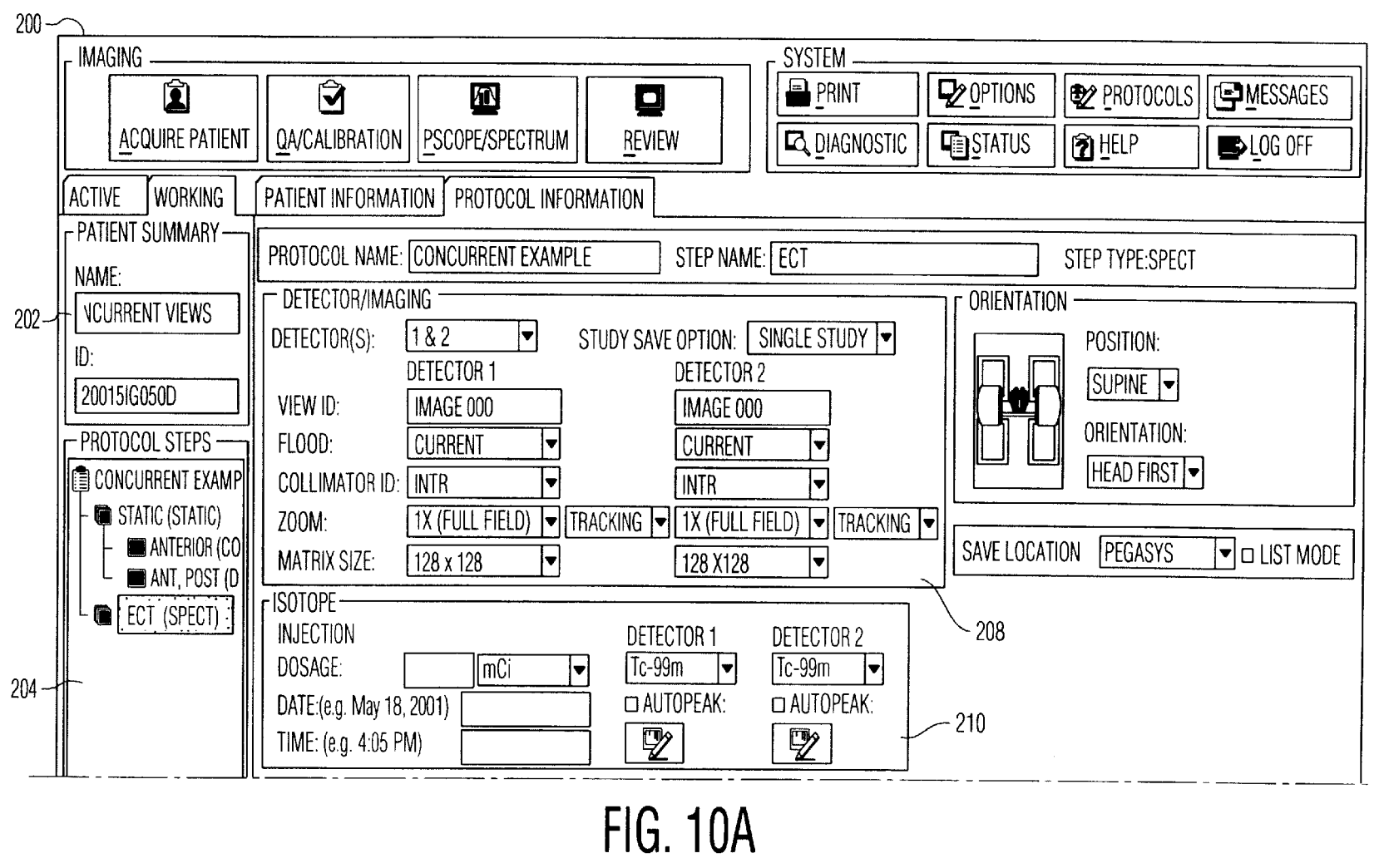
Figure 10B:
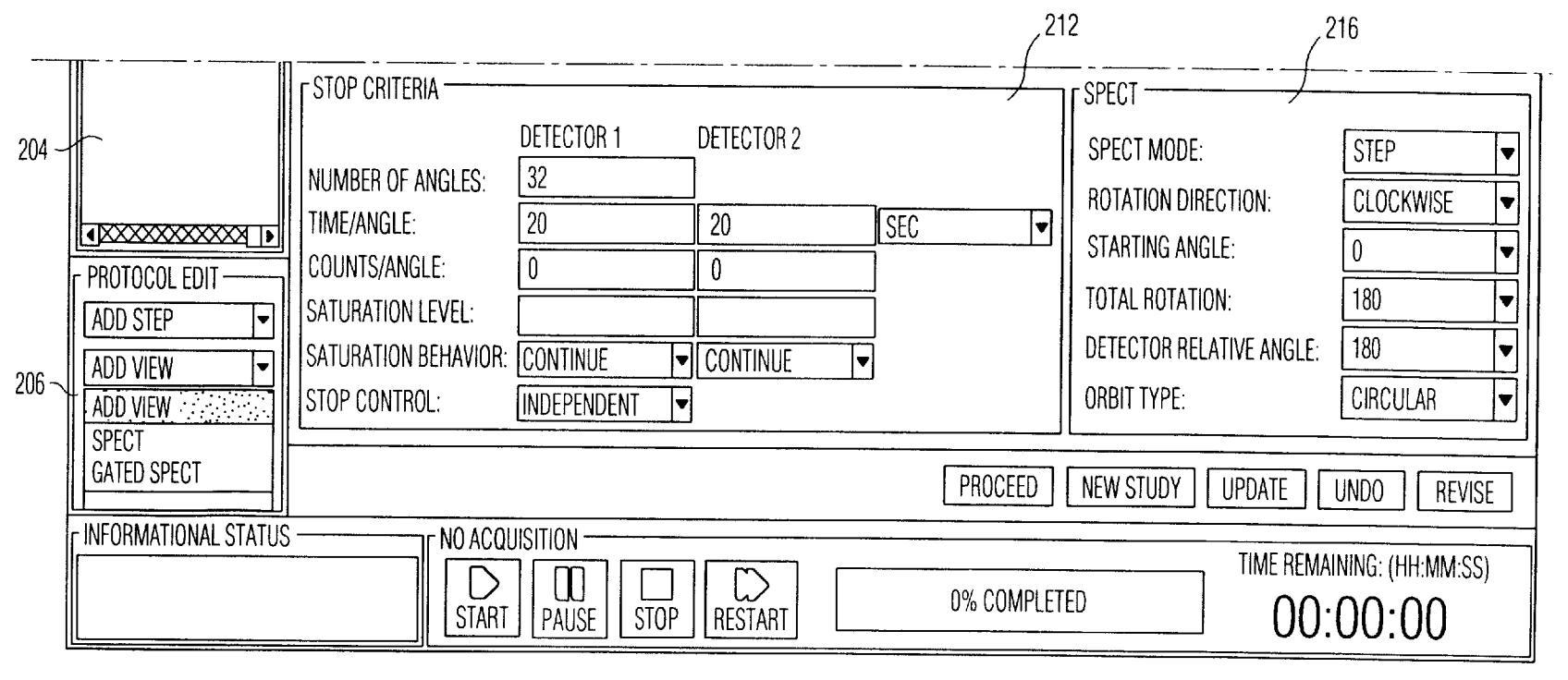

In FIG. 10 the operator has highlighted the SPECT step in the protocol box 204, and details of this step of the protocol appear in the central boxes 208–212. In addition, a SPECT box 216 is displayed showing information particular to detector head movement (gantry operation) during the SPECT step of the protocol. When the user pulls down the "Add View" menu in box 206 to add another view to this step, the choices of "SPECT" (non-gated SPECT) and "Gated SPECT", which are compatible with the SPECT step are displayed to the operator for selection.

Figures 11, 11A, 11B:
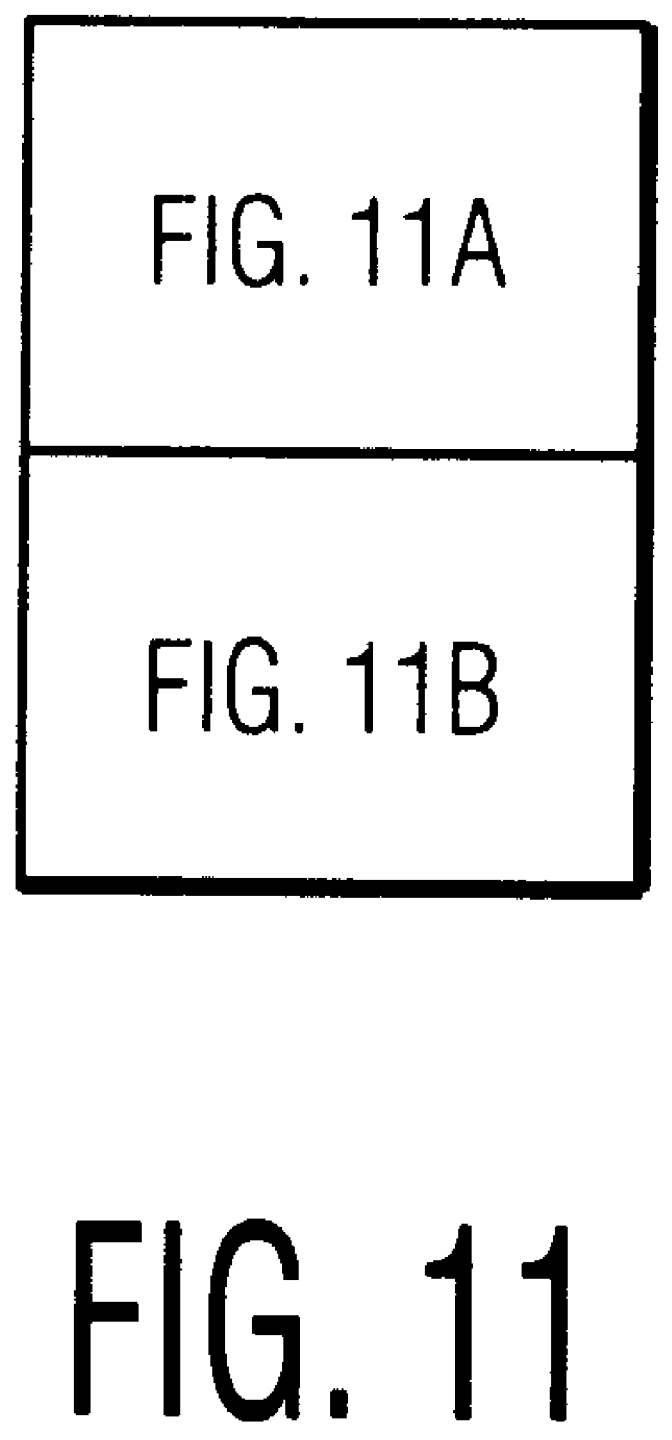
Figure 11A:
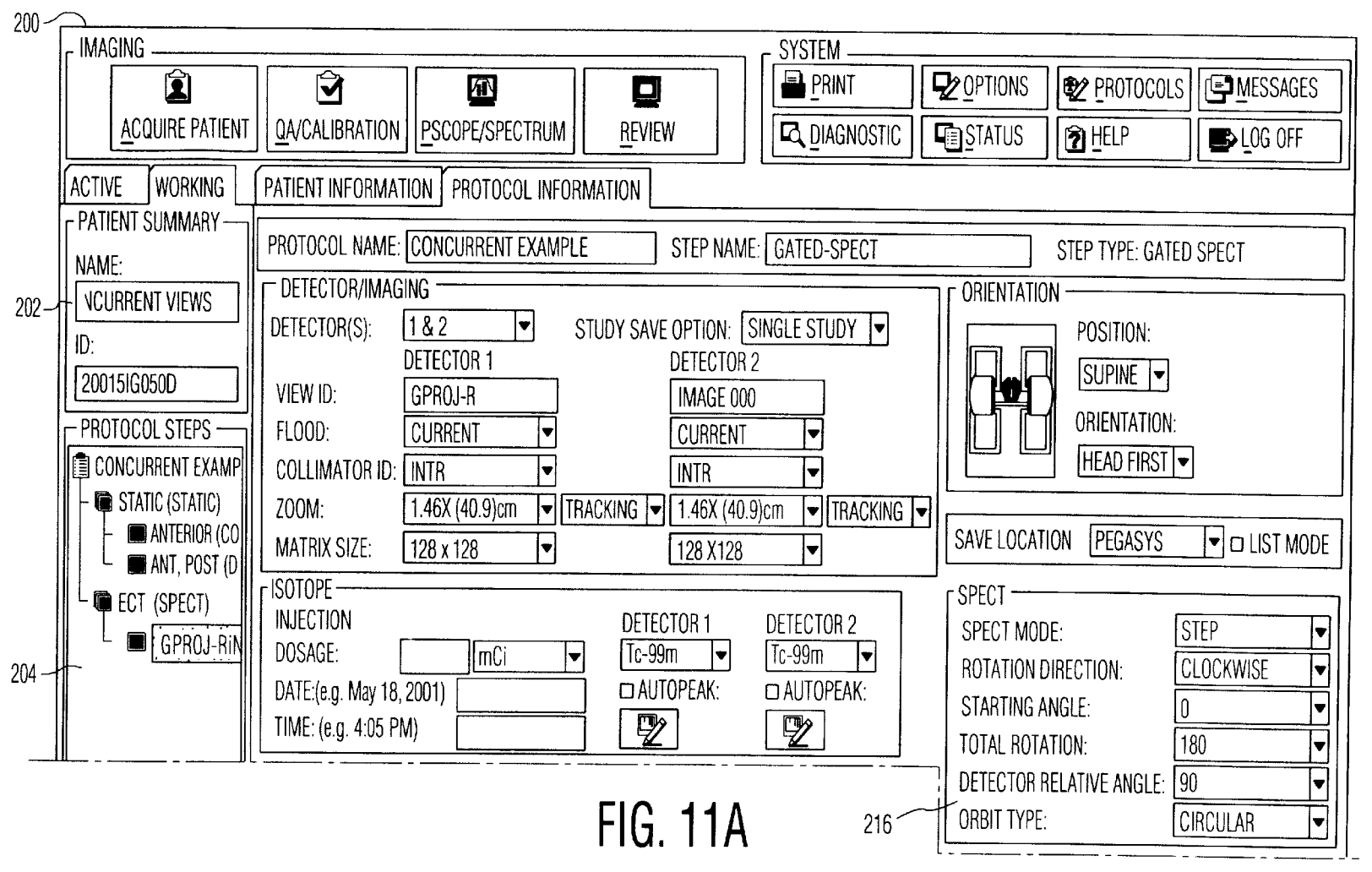
Figure 11B:
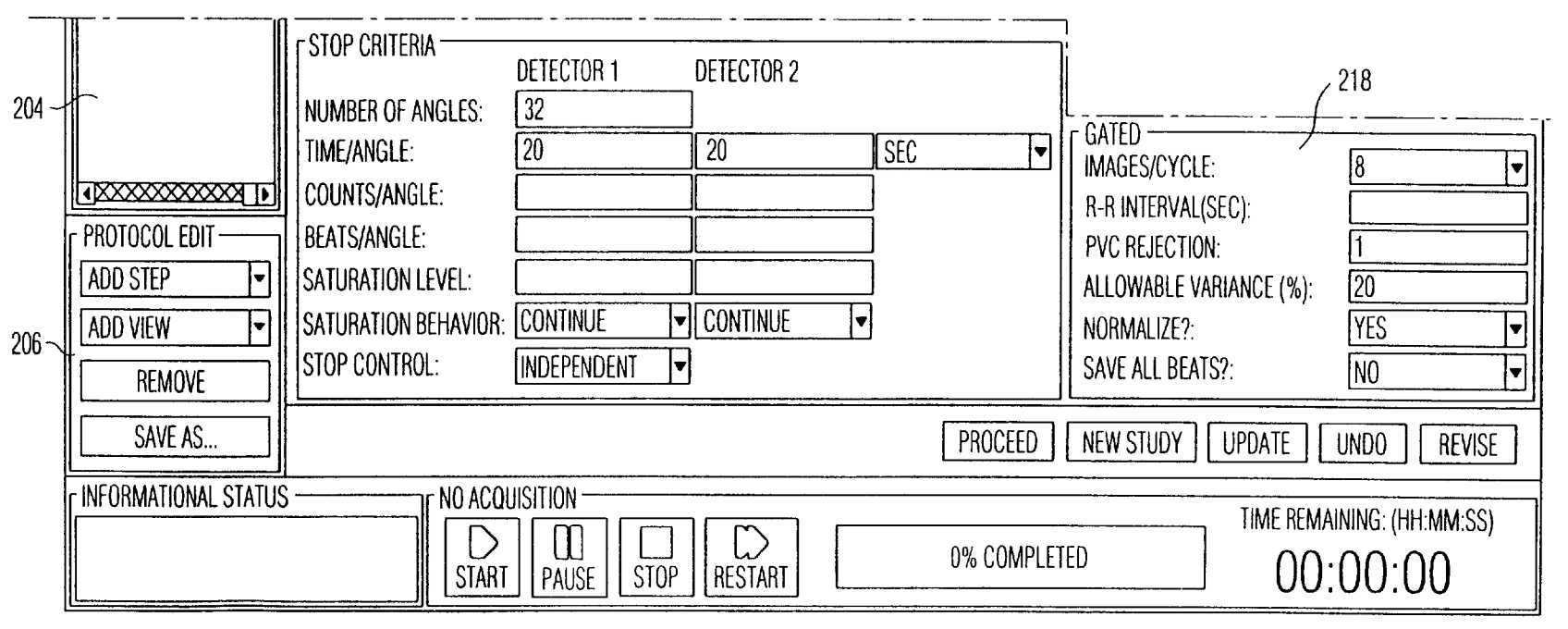

In FIG. 11 the operator has added a gated SPECT view to the SPECT step, as shown by the highlighted view line "GPROJ-R" in the protocol box 204. Parameters of the gating may be set in the "Gated" box 218 which now appears for the operator. The camera is now set up to perform both a gated and a non-gated acquisition simultaneously as described above.

Figure 12A:
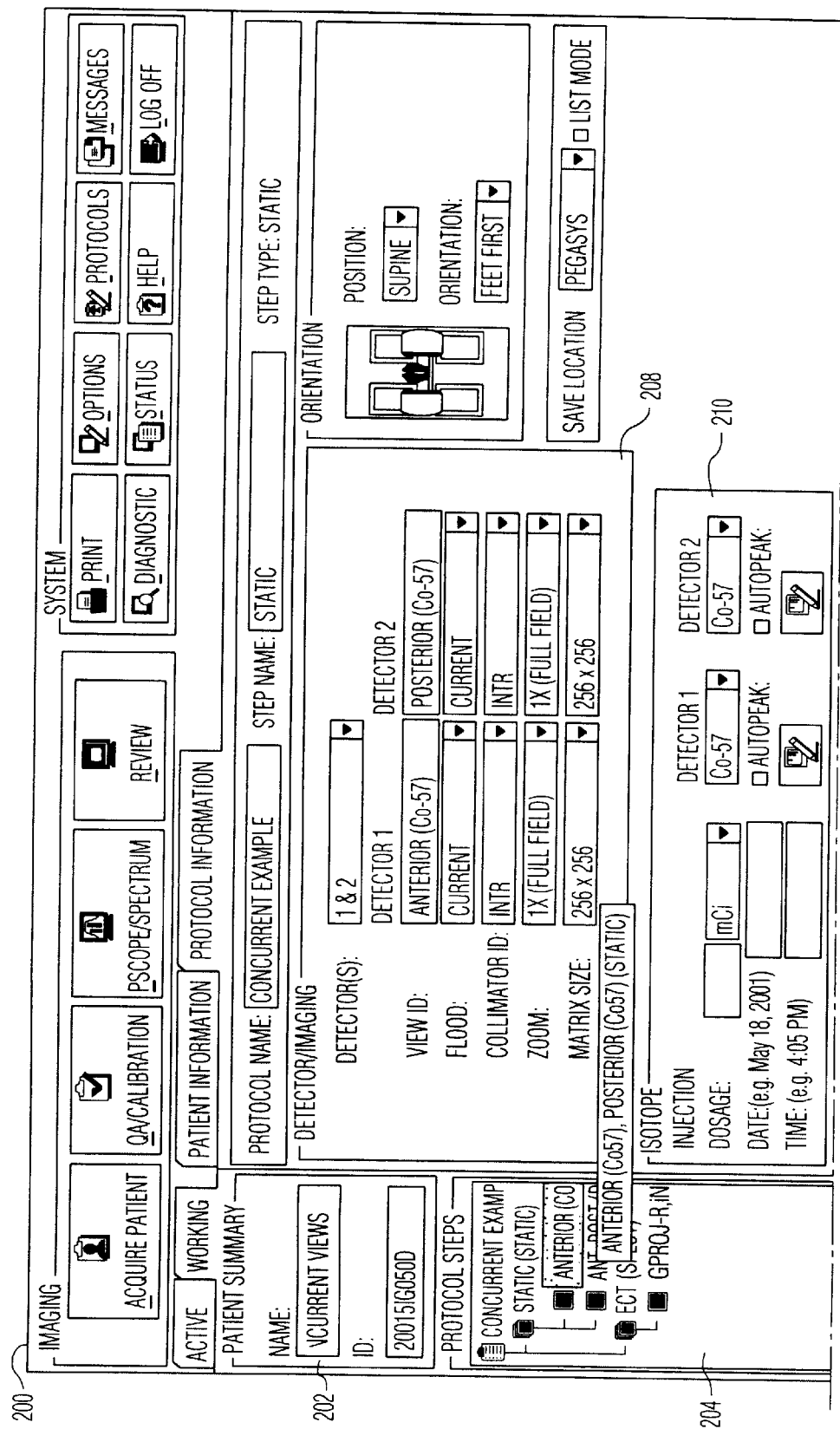
Figure 12B:
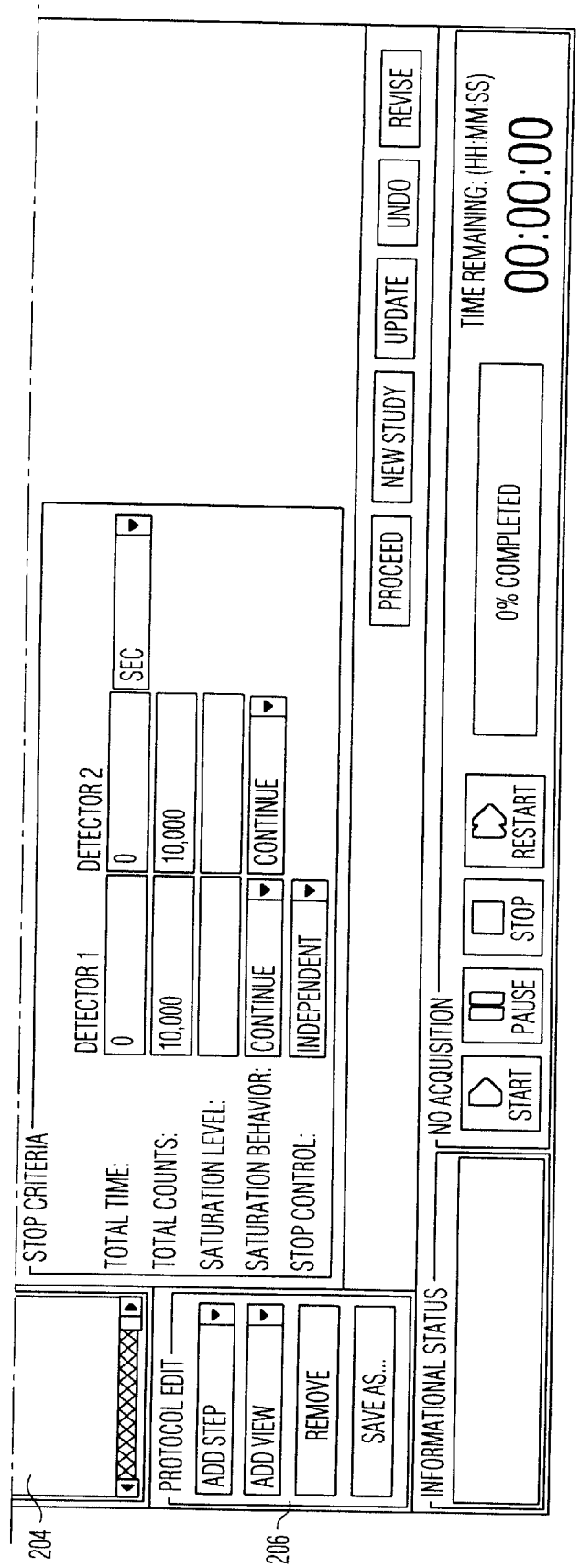

FIG. 12 shows the simultaneous acquisitions of the static step being set up for multi-energy operation. As the Isotope box 210 shows, event data of the isotope Co-57 is being acquired in one view while the parent static step is acquiring event data of the isotope Tc-99m (see FIG. 7). Thus, views from different isotopes can be set up and acquired simultaneously through the user interface 200.

It is seen that an embodiment of the present invention can allow a clinician to set up protocols of multiple steps and with the acquisition of multiple simultaneous views. Energy windows can be turned on and off or edited for any step and isotopes can be set up for any step. Concurrent acquisition of different energy windows allows energy windows to be combined and images of specific combinations of energy windows to be produced. As the clinician sets up the desired protocol the user interface disables conflicting parameters so that validly executable protocols result.

What is claimed is:

1. A nuclear camera system comprising:
   a detector coupled to a gantry;
   a controller, coupled to the gantry and detector, which controls operation of the gantry and detector in accordance with a study protocol; and
   a user interface, coupled to the controller, which enables the setup of a study protocol for performing different types of acquisitions concurrently.

2. The nuclear camera system of claim 1, wherein the user interface further acts to prevent the setup of concurrent acquisitions which are incompatible with each other.

3. The nuclear camera system of claim 1, wherein the concurrent acquisitions are gated SPECT and non-gated SPECT acquisitions.

4. The nuclear camera system of claim 1, wherein the concurrent acquisitions are a static acquisition and one of a dynamic, static, and gated planar acquisition.

5. The nuclear camera system of claim 1, wherein the user interface further comprises a display which displays the steps selected for a protocol and the views selected for each step.

6. The nuclear camera system of claim 5, wherein the user interface further comprises a control by which at least one of an additional step or an additional view can be added to the protocol.

7. The nuclear camera system of claim 6, wherein the user interface control comprises a pull-down menu which prevents the addition of an incompatible step or view to the protocol.

8. The nuclear camera system of claim 7, wherein the pull-down menu further comprises selections of only compatible additions to a step or view.

9. The nuclear camera system of claim 7, wherein the pull-down menu further comprises grayed-out selections which are incompatible with the step or view being modified.

10. The nuclear camera system of claim 1, wherein the user interface comprises means for enabling a user to produce a protocol for acquiring two event data sets during the same acquisition step; and
    wherein the means for enabling further comprises means for checking that acquisition of the two data sets is consistent with the gantry behavior of the acquisition step.

11. A method for setting up a study protocol for a first study for a gamma camera having a camera controller and a user interface coupled to the camera controller comprising:
    displaying a list of steps for a second study which may be added to the protocol for the first study;
    displaying a list of views which may be added to a step of the protocol;
    enabling the selection of steps for the second study to be added to the protocol for simultaneous acquisition with the first study; and
    enabling the selection of multiple views which may be acquired during a step of the protocol.

12. The method of claim 11, further comprising:
    preventing the selection of multiple incompatible views for simultaneous acquisition.

13. The method of claim 12, further comprising:
    displaying the steps and multiple simultaneous views chosen for a protocol.

* * * * *